United States Patent
Weitkemper et al.

(12) 
(10) Patent No.: US 6,383,514 B1
(45) Date of Patent: May 7, 2002

(54) USE OF MIXTURES OF ACTIVE SUBSTANCES FOR THE PRODUCTION OF HYPOCHOLESTEROLEMIC AGENTS

(75) Inventors: Norbert Weitkemper, Leverkusen; Bernd Fabry, Korschenbroich, both of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/308,512

(22) PCT Filed: Nov. 19, 1997

(86) PCT No.: PCT/EP97/06447

§ 371 Date: May 20, 1999

§ 102(e) Date: May 20, 1999

(87) PCT Pub. No.: WO98/23275

PCT Pub. Date: Jun. 4, 1998

(30) Foreign Application Priority Data

Nov. 28, 1996 (DE) .......................................... 196 49 286
Jan. 13, 1997 (DE) .......................................... 197 00 796

(51) Int. Cl.⁷ ................................................. A61K 9/48
(52) U.S. Cl. ....................... 424/456; 424/430; 424/436; 424/451
(58) Field of Search ............................ 424/430, 436, 424/451, 456

(56) References Cited

U.S. PATENT DOCUMENTS

| | | | |
|---|---|---|---|
| 3,085,939 A | 4/1963 | Wruble et al. ................ | 167/65 |
| 3,089,939 A | 5/1963 | Dunlap et al. ................ | 219/19 |
| 3,203,862 A | 8/1965 | Jones et al. .................. | 167/65 |

FOREIGN PATENT DOCUMENTS

| | | |
|---|---|---|
| CA | 928140 | 6/1973 |
| CA | 2 101 079 | 8/1984 |
| CA | 1 185 500 | 4/1985 |
| DE | 20 35 069 | 1/1971 |
| DE | 43 23 615 | 1/1995 |
| EP | 0 195 311 | 9/1986 |
| EP | 0 289 636 | 11/1988 |
| FR | 2 511 253 | 7/1983 |
| FR | 2 620 024 | 3/1989 |
| FR | 2 701 266 | 8/1994 |
| JP | 57 206336 | 12/1982 |
| WO | WO92/19640 | 11/1992 |
| WO | WO94/01413 | 1/1994 |
| WO | WO94/14419 | 7/1994 |
| WO | WO95/01773 | 1/1995 |
| WO | WO96/16991 | 6/1996 |

OTHER PUBLICATIONS

Chemical Abstracts, vol. 79, No. 13, (1973) XP002061647.
Eiyo To Shokuryo, vol. 26, (1973) pp. 27–32.
Patent Abstracts of Japan, vol. 007, No. 056, (1983).
J.Nutrit., vol. 50. (1953) pp. 191–201.
Ullmann's Encyclopedia of Industrial Chemistry, vol. 6, (1986) pp. 231–332.
Happi, vol. 27, (1990) p. 57.
Drug Cosmetic Ind., vol. 148, (1991) pp. 24–30.
Seifen–Ole–Fette–Wachse, vol. 117, (1991) pp. 633–637.
Makromol Chem., vol. 177, (1976) pp. 3589–3600.
J.Am.Chem.Soc., vol. 63, (1941) pp. 1259–1261.

*Primary Examiner*—James M. Spear
(74) *Attorney, Agent, or Firm*—John E. Drach; Steven J. Trzaska

(57) ABSTRACT

A hypocholesterolemic composition, for use in reducing serum cholesterol levels in warm-blooded organisms, the composition containing: (a) a phytostanol ester and (b) a tocopherol.

20 Claims, No Drawings

USE OF MIXTURES OF ACTIVE SUBSTANCES FOR THE PRODUCTION OF HYPOCHOLESTEROLEMIC AGENTS

This application is a 371 of PCT/EP97/06447 filed Nov. 19, 1997.

BACKGROUND OF THE INVENTION

This invention relates to the use of mixtures of phytostanol esters and tocopherols for the production of preparations for reducing the serum cholesterol level of warm-blooded organisms.

Hypocholesterolemic agents are understood to be agents which lead to a reduction in the serum cholesterol level of warm-blooded organisms without either inhibiting or reducing the formation of cholesterol in the blood. Phytosterols, i.e. vegetable sterols, and esters thereof with fatty acids have already been proposed for this purpose by Peterson et al. in J. Nutrit. 50, 191 (1953). U.S. Pat. Nos. 3,089,939, 3,203, 862 and DE-OS 2 035 069 (Procter & Gamble) also point in the same direction. The active substances are normally added to frying oils or edible oils and, accordingly, are absorbed through the food. However, the quantities used are generally minimal and, normally, amount to less than 0.5% by weight to prevent the edible oils from clouding or the sterols from precipitating on the addition of water. For use in foods, in cosmetics, in pharmaceutical preparations and in the agricultural sector, storable emulsions of the sterol esters in sugar or polyglycerol esters are proposed in European patent application EP-A1 0 289 636 (Ashai). The incorporation of sitostanol esters in margarine, butter, mayonnaise, salad creams and the like for reducing the blood cholesterol level is proposed in European patent EP-B1 0594612 (Raision).

Unfortunately, a disadvantage of phytostanol esters is that, normally, they can only be added to foods in small quantities because otherwise they are in danger of affecting the taste and/or consistency of foods. However, if the blood cholesterol level is to be lastingly influenced, relatively large quantities of phytostanol esters would have to be absorbed. The rate at which the substances reduce serum cholesterol is also in need of improvement. Accordingly, the problem addressed by the present invention was to remedy these deficiencies.

DESCRIPTION OF THE INVENTION

The present invention relates to the use of mixtures of active substances for the production of hypocholesterolemic preparations, characterized in that (a) phytostanol esters and
(b) tocopherols are used.

It has surprisingly been found that tocopherols, which have no hypocholesterolemic properties of their own, act as potentiating agents for phytostanol esters, i.e. accelerate the reduction of the serum cholesterol level in the presence of phytostanol esters. In addition, when encapsulated in gelatine, the active-substance mixtures can readily be taken in by mouth.

Phytostanol Esters

Phytostanol (also known as phytosterols) are vegetable steroids which only contain a hydroxyl group but no other functional groups at C-3. In general, phytosterols contain 27 to 30 carbon atoms and one double bond in the 5/6 position and occasionally in the 7/8, 8/9 or other positions. The phytostanols which form component (a) after esterification with fatty acids are obtained from the phytostenols by hydrogenation. The phytostanol component can be derived from the hydrogenation products of ergosterols, campesterols, stigmasterols, brassicasterols, preferably sitosterols and, more particularly, β-sitostanols. The acid component of the ester may go back to carboxylic acids corresponding to formula (I):

$$R^1CO\text{—}OH \tag{I}$$

in which $R^1CO$ is an aliphatic, linear or branched acyl group containing 2 to 22 carbon atoms and 0 and/or 1, 2 or 3 double bonds. Typical examples are acetic acid, propionic acid, butyric acid, valeric acid, caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeosteric acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example cocofatty acid, palm oil fatty acid, palm kernel oil fatty acid or tallow fatty acid, are preferred. It is particularly preferred to use esters of β-sitostanol with fatty acids containing 12 to 18 carbon atoms. These esters may be prepared both by direct esterification of the phytostanols with the fatty acids or by transesterification with fatty acid lower alkyl esters or triglycerides in the presence of suitable catalysts, for example sodium ethylate or, more particularly, enzymes [cf. EP-A2 0195311 (Yoshikawa)]. The corresponding phytostenol esters may also be initially prepared and then hydrogenated with the carbonylester group in tact.

Tocopherols

Tocopherols are chroman-6-ols (3,4-dihydro-2-H-1-benzopyran-6-ols) substituted in the 2-position by 4,8,12-trimethyltridecyl groups which correspond to formula (II):

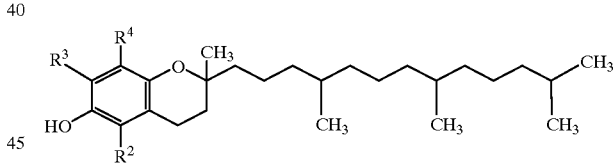

(II)

in which $R^2$, $R^3$ and $R^4$ independently of one another represent hydrogen or a methyl group. Tocopherols belong to the bioquinones, i.e. polyprenylated 1,4-benzo- or naphthoquinones of which the prenyl chains are more or less heavily saturated. Typical examples of tocopherols suitable for use as component (b) in accordance with the invention are ubiquinones, boviquinones, K-vitamins and/or menaquinones (2-methyl-1,4-naphthoquinones). Other tocopherols include α-, β-, γ-, δ- and ε-tocopherols, the latter still having the original unsaturated prenyl side chain, and α-tocopherolquinone and hydroquinone where the pyran ring system is opened. α-Tocopherol (vitamin E) corresponding to formula (II), in which $R^2$, $R^3$ and $R^4$ represent methyl groups, or esters of α-tocopherol with carboxylic acids containing 2 to 22 carbon atoms, such as for example α-tocopherol acetate or α-tocopherol palmitate, are preferably used as component (b).

Chitosans

The preparations may contain chitosans (component c1) as further potentiating agents. Citosans are biopolymers which belong to the group of hydrocolloids. Chemically, they are partly deacetylated chitins differing in their molecular weights which contain the following—idealized—monomer unit (III):

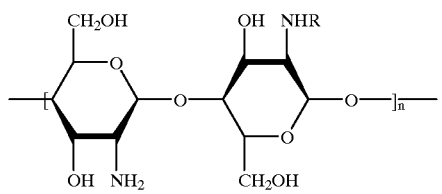

(III)

In contrast to most hydrocolloids, which are negatively charged at biological pH values, chitosans are cationic biopolymers under these conditions. The positively charged chitosans are capable of interacting with oppositely charged surfaces and are therefore used in cosmetic hair care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), by O. Skaugrud in Drug Cosm. Ind. 148, 24 (1991) and by E. Onsoyen et al. in Seifen-Öle-Fette-Wachse 117 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR-A 2701266. A preferred embodiment of the invention is characterized by the use of the chitin degradation product described in International patent application WO 96/16991 (Henkel) or the degradation product thereof with hydrogen peroxide.

Phytosterol Sulfates

The preparations may contain phytosterol sulfates as further potentiating agents (component c2). Phytosterol sulfates are known substances which may be obtained, for example, by sulfation of phytosterols with a complex of sulfur trioxide and pyridine in benzene [cf. J. Am. chem. Soc. 63, 1259 (1941)]. Typical examples are the sulfates or ergosterols, campesterols, stigmasterols and sitosterols. The phytosterol sulfates may be used in the form of alkali metal and/or alkaline earth metal salts, ammonium, alkylammonium, alkanolammonium and/or glucammonium salts. They are generally used in the form of their sodium salts.

(Deoxy)ribonucleic Acids

Finally, the preparations may contain (deoxy)ribonucleic acids as further potentiating agents (component c3). (Deoxy) ribonucleic acids (DNA, RNA) are understood to be high molecular weight filament-like polynucleotides which are derived from 2'-deoxy-$\beta$-D-ribonucleosides or D-ribonucleosides which, in turn, are prepared from equivalent quantities of a nucleobase and the pentose 2-deoxy-D-ribofuranose or D-ribofuranose. The DNA or RNA may contain the purine derivatives adenine and guanine and the pyrimidines cytosine and thymine or uracil as nucleobases. In the nucleic acids, the nucleobases are attached by an N-glycosidic bond to carbon atom 1 of the ribose, so that adenosines, guanosines, cytidines and thimidines are formed in the particular individual case. In the acids, a phosphate group attaches the 5'-hydroxy group of the nucleosides to the 3'-OH group of the following phosphate group by a phosphodiester bridge to form single-stranded DNA or RNA. In view of the considerable length-to-diameter ratio, DNA or RNA molecules show a tendency towards strand breakage even under mechanical stressing, for example during extraction. For this reason, the molecular weight of the nucleic acids can reach $10^3$ to $10^9$ dalton. Concentrated DNA or RNA solutions, which are distinguished by liquid crystalline behavior, are used for the purposes of the invention. (Deoxy) ribonucleic acids which are obtained from marine sources, for example by extraction of fish sperm, and which have a molecular weight of 40,000 to 1,000,000 dalton are preferably used.

Commercial Applications

The active-substance mixtures according to the invention may contain the phytostanol esters and the tocopherols in a ratio by weight of 99:1 to 1:99, preferably 90:10 to 10:90, more preferably 70:25 to 25:75 and most preferably 60:40 to 40:60, the only important requirement being to ensure that a quantity of component (a) sufficient to lower the blood cholesterol level is taken up through the use according to the invention. In one particular embodiment of the invention, the active-substance mixtures are encapsulated in known manner in gelatine, components (a) and (b) each being used in quantities of 0.1 to 50% by weight, preferably in quantities of 1 to 30% by weight, more preferably in quantities of 5 to 25% by weight and most preferably in quantities of 10 to 15% by weight, based on the weight of the gelatine capsules. The encapsulation of the phytostanol esters in gelatine—alone or in admixture with the potentiating agents—represents an advantageous embodiment for the oral administration of the active substances. The percentage content of the other potentiating agents (component c) may be from 1 to 10% by weight, based on the active-substance mixtures.

Another form of administration of the active-substance mixtures are suppositories which may be inserted rectally or vaginally and which may also contain gelatine, optionally in combination with glycerol, or even synthetic fats or waxes, polyethylene glycols or natural constituents, for example cocoa butter, as the suppository base. The mixtures may also be dissolved or dispersed in normal foods, for example salad oils, dressings, mayonnaises, margarines, butter, frying fats, cocoa products, sausage and the like.

EXAMPLES

Examples 1 to 4, Comparison Examples C1 to C4

Gelatine capsules (weight ca. 1.5 g) containing $\beta$-sitostanol or $\beta$-sitostenol sitostenol esters and optionally tocopherol and 0.5% by weight of radioactively labeled cholesterol were prepared. To investigate the hypocholesterolemic effect, male rats (each weighing ca. 200 g) were kept off food overnight. On the following day, a size-reduced gelatine capsule was inserted into each test animal with a little salt-containing water through a stomach probe. After 3, 6, 12, 24 and 48 h, blood was removed from the animals and the content of radioactive cholesterol was determined. The results—which represent the average value of the measurements of 10 test animals—are set out in Table 1 below. The data relating to the reduction in radioactivity are based on a control group of test animals which were only given gelatine capsules containing 20% by weight of vitamin E and a corresponding quantity of radioactively labeled cholesterol. Mixtures 1 to 4 correspond to the invention while mixtures C1 to C4 are intended for comparison.

TABLE 1

Hypocholesterolemic effect (quantities in % by weight, based on gelatine capsule)

| Composition/activity | C1 | 1 | 2 | 3 | 4 | C2 | C3 | C4 |
|---|---|---|---|---|---|---|---|---|
| Lauric acid-β-sitostanol ester | 0 | 3 | 5 | 7 | 9 | 10 | 5 | — |
| Lauric acid-β-sitostenol ester | — | — | — | — | — | — | — | 5 |
| Vitamin E | 10 | 7 | 5 | 3 | 1 | 0 | 0 | 0 |
| Radioactivity [%-rel] | | | | | | | | |
| after 3 h | 100 | 94 | 94 | 95 | 95 | 91 | 95 | 95 |
| after 6 h | 100 | 85 | 82 | 81 | 80 | 79 | 84 | 86 |
| after 12 h | 100 | 76 | 71 | 69 | 67 | 67 | 76 | 79 |
| after 24 h | 100 | 45 | 43 | 39 | 40 | 40 | 51 | 57 |
| after 48 h | 100 | 28 | 23 | 25 | 20 | 21 | 30 | 39 |

Discussion of the Results

Tocopherol on its own has no hypocholesterolemic activity (Example C1)

A mixture of 9% by weight sitostanol ester and 1% by weight tocopherol has the same effect as using 10% by weight sitostanol ester (Examples 4 and C2)

A mixture of 5% by weight sitostanol ester and 5% by weight tocopherol is far more active than 5% by weight sitostanol ester alone (Examples 2 and C3); it is comparable in its activity with 10% by weight sitostanol ester alone (Example C2).

What is claimed is:

1. A hypocholesterolemic composition comprising:
   (a) a phytostanol ester and
   (b) a tocopherol.

2. The composition of claim 1 wherein the phytostanol ester is a β-sitostanol ester.

3. The composition of claim 2 wherein the β-sitostanol ester is formed using a carboxylic acid corresponding to formula (I):

$$R^1CO\text{—}OH \quad (I)$$

wherein $R^1CO$ is an aliphatic, linear or branched alkyl group having from 2 to 22 carbon atoms, and up to 3 double bonds.

4. The composition of claim 3 wherein in formula (I), wherein $R^1CO$ is an aliphatic, linear or branched alkyl group having from 12 to 18 carbon atoms, and up to 3 double bonds.

5. The composition of claim 1 wherein the tocopherol is α-tocopherol.

6. The composition of claim 1 further comprising a potentiating agent selected from the group consisting of a chitosan, a phytosterol sulfate, a (deoxy)ribonucleic acid, and mixtures thereof.

7. The composition of claim 6 wherein the potentiating agent is present in the composition in an amount of from 1 to 10% by weight, based upon the weight of the composition.

8. The composition of claim 1 wherein (a) and (b) are present in a ratio by weight of from 60:40 to 40:60.

9. The composition of claim 1 wherein the hypocholesterolemic composition is contained in a gelatine capsule.

10. The composition of claim 9 wherein the hypocholesterolemic composition is present in the gelatine capsule in an amount of from 0.1 to 50% by weight, based on the weight of the gelatine capsule.

11. A process for reducing serum cholesterol levels in warm-blooded organisms comprising administering an effective amount of a hypocholesterolemic composition to the warm-blooded organism, the hypocholesterolemic composition containing:
   (a) a phytostanol ester and
   (b) a tocopherol.

12. The process of claim 11 wherein the phytostanol ester is a β-sitostanol ester.

13. The process of claim 12 wherein the β-sitostanol ester is formed using a carboxylic acid corresponding to formula (I):

$$R^1CO\text{—}OH \quad (I)$$

wherein $R^1CO$ is an aliphatic, linear or branched alkyl group having from 2 to 22 carbon atoms, and up to 3 double bonds.

14. The process of claim 13 wherein in formula (I), wherein $R^1CO$ is an aliphatic, linear or branched alkyl group having from 12 to 18 carbon atoms, and up to 3 double bonds.

15. The process of claim 11 wherein the tocopherol is α-tocopherol.

16. The process of claim 11 wherein the composition further contains a potentiating agent selected from the group consisting of a chitosan, a phytosterol sulfate, a (deoxy) ribonucleic acid, and mixtures thereof.

17. The process of claim 16 wherein the potentiating agent is present in the composition in an amount of from 1 to 10% by weight, based upon the weight of the composition.

18. The process of claim 11 wherein (a) and (b) are present in the composition in a ratio by weight of from 60:40 to 40:60.

19. The process of claim 11 wherein the hypocholesterolemic composition is administered orally, rectally or vaginally.

20. The process of claim 11 wherein the hypocholesterolemic composition is administered orally in a gelatine capsule containing from 0.1 to 50% by weight of the hypocholesterolemic composition, based on the weight of the gelatine capsule.

* * * * *